United States Patent [19]

Magee

[11] 4,299,783
[45] Nov. 10, 1981

[54] 1-ALKYLSULFONYL-3-SUBSTITUTED PHOSPHINYLTHIO- OR PHOSPHINOTHIOYLTHIO-PROPENES

[75] Inventor: Philip S. Magee, Vallejo, Calif.

[73] Assignee: Chevron Research Company, San Francisco, Calif.

[21] Appl. No.: 143,984

[22] Filed: Apr. 28, 1980

[51] Int. Cl.³ .................. C07F 9/165; A01N 37/12
[52] U.S. Cl. ............................. 260/948; 71/87; 424/216
[58] Field of Search .................. 260/948; 424/216

[56] References Cited

U.S. PATENT DOCUMENTS

| | | | |
|---|---|---|---|
| 2,864,740 | 12/1958 | Diveley | 260/948 |
| 2,898,341 | 8/1959 | Sehring et al. | 260/948 |
| 2,952,700 | 9/1960 | Lorenz et al. | 260/948 |
| 3,153,664 | 10/1964 | Schicke et al. | 260/948 |
| 3,716,600 | 2/1973 | Magee | 260/948 |
| 3,742,098 | 6/1973 | Oswald et al. | 260/948 |
| 3,801,680 | 4/1974 | Magee | 260/948 |
| 3,825,634 | 7/1974 | Magee | 260/959 |
| 3,845,172 | 10/1974 | Magee | 424/220 |
| 3,868,449 | 2/1975 | Magee | 424/220 |
| 3,885,032 | 5/1975 | Magee | 424/220 |
| 3,914,417 | 10/1975 | Magee | 425/220 |
| 4,110,443 | 8/1978 | Magee | 424/220 |
| 4,192,829 | 3/1980 | Oswald et al. | 260/948 |

*Primary Examiner*—Anton H. Sutto
*Attorney, Agent, or Firm*—D. A. Newell; T. G. DeJonghe; L. S. Squires

[57] ABSTRACT

3-Phosphinylthio- and 3-phosphinothioylthio-1-sulfonyl propenes have fungicidal and insecticidal activity.

4 Claims, No Drawings

1-ALKYLSULFONYL-3-SUBSTITUTED PHOSPHINYLTHIO- OR PHOSPHINOTHIOYLTHIO-PROPENES

BACKGROUND OF THE INVENTION

U.S. Pat. Nos. 3,716,600, 3,801,680, 3,825,634, 3,845,172, 3,868,449, 3,885,032, 3,914,417, 4,049,679 and 4,110,443 disclose insecticidal O-alkyl-S-alkenyl-N-alkanoyl-phosphoramidothioates and dithioates.

SUMMARY OF THE INVENTION

I have now found that 3-substituted-1-alkylsulfonyl-propenes, 1-cycloalkylsulfonylpropenes, 1-alkenylsulfonyl-propenes and 1-alkynylsulfonylpropenes wherein the 3-substituents are particular phosphinylthio- or phosphinothioylthio-groups are effective for the control of fungi and insects.

The compounds of the invention are particularly effective against aphids, houseflies, American cockroaches, rootworms, cabbage loopers and Yellow Fever mosquitoes. As fungicides, the compounds of the invention are particularly effective against *Plasmopara viticola*, *Septoria apii* and *Alternaria solari*.

DESCRIPTION OF THE INVENTION

The compounds of the invention are represented by the formula (I):

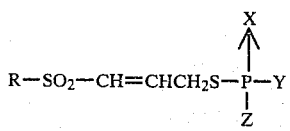

wherein R is alkyl of 1 to 6 carbon atoms, cycloalkyl of 5 to 10 carbon atoms, alkenyl of 2 to 6 carbon atoms, alkynyl of 2 to 6 carbon atoms, all of said R groups being optionally substituted with from 1 to 13 halogen atoms; X is oxygen or sulfur:

Y is $-OR^1$ or $-SR^1$ wherein $R^1$ is selected from the same groups which define R above;

Z is $-OR^2$, $-SR^2$, alkyl of 1 to 6 carbon atoms, aryl of 6 to 10 carbon atoms, or the group $-NR'R''$ wherein $R^2$ is selected from the same groups which define R above, and R' and R'' are independently hydrogen, alkyl of 1 to 6 carbon atoms or acyl of 2 to 6 carbon atoms.

Representative R alkyl groups are methyl, ethyl, n-propyl, i-propyl, n-butyl, i-butyl, sec-butyl, t-butyl, n-pentyl, i-pentyl, neo-pentyl, n-hexyl, i-hexyl. Representative R cycloalkyl groups are cyclopentyl, cyclohexyl, cycloheptyl and cyclooctyl. Representative R alkenyl groups are vinyl, allyl, prop-1-enyl, i-propenyl, 2,2-dimethyl vinyl, but-2-enyl, but-3-enyl, but-1-enyl, i-butenyl, 3-methyl-pent-1-enyl, pent-2-enyl, hex-1-enyl, 3,3-dimethyl-but-1-enyl and 1,2,2-trimethyl-pro-1-enyl. Representative R alkynyl groups are ethynyl, prop-1-ynyl, prop-2-ynyl, but-1-ynyl and but-2-ynyl. Representative halo-substituted R groups are chloromethyl, trifluoromethyl, 1,1,2,2-tetrabromoethyl, 4-chlorocyclohexyl, 2,4,6-trichlorocyclohexyl, trichlorovinyl, pentabromoallyl, 3,3-dichlorovinyl and 3,3,3-trifluoro prop-1-ynyl.

Representative Z groups are methoxy, ethoxy, i-propoxy, n-propoxy, n-butoxy, i-butoxy, sec-butoxy, methylmercapto, ethylmercapto, i-propylmercapto, n-propylmercapto, cyclohexyloxy, cyclohexylmercapto, but-3-enoxy, but-3-enmercapto, propargyloxy, propargylmercapto, methyl, ethyl, i-propyl, n-propyl, n-butyl, i-butyl, sec-butyl, n-pentyl, i-pentyl, neo-pentyl, n-hexyl, i-hexyl, phenyl, 1-methylnaphth-1-yl, p-chlorophenyl, p-nitrophenyl, 2,4-dichlorophenyl, 2,4,6-trimethylphenyl, amino, methylamino, dimethylamino, methylethylamino, di-n-butylamino, di-n-hexylamino, acetamido, propionamido, butyramido and valeramido.

Preferably R is alkyl of 1 to 6 carbon atoms or cycloalkyl of 5 to 10 carbon atoms. More preferably R is alkyl of 1 to 6 carbon atoms. Most preferably R is methyl or iso-butyl.

Preferably X is oxygen.

Preferably Y is alkoxy of 1 to 6 carbon atoms. Most preferably Y is methoxy.

Preferably Z is alkoxy of 1 to 6 carbon atoms, alkylthio of 1 to 6 carbon atoms, alkyl of 1 to 6 carbon atoms, aryl of 6 to 10 carbon atoms or amino. More preferably, Z is alkoxy of 1 to 6 carbon atoms or amino.

The compounds of the invention may be made according to the following scheme:

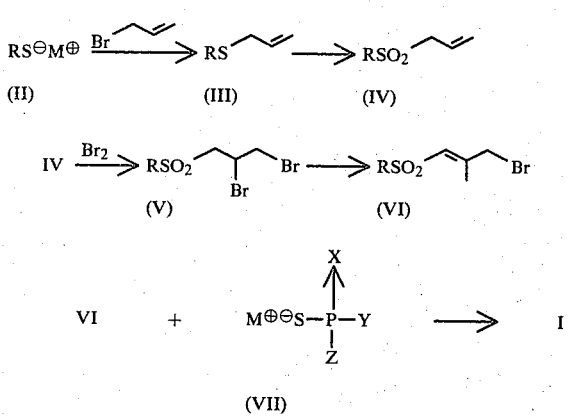

wherein R, X, Y and Z are as previously defined and $M\oplus$ is a monovalent cation, such as $Na\oplus$, $K\oplus$, $Li\oplus$, $NH\oplus_4$.

The sequence of procedures starting from the alkyl sulfide salt (II) and terminating with the sulfonyl propenyl bromide (VI) involve conventional reaction conditions. Substantially equimolar amounts of the alkyl sulfide salt (II) and allyl bromide are reacted in a solvent at from 0°–40° C. The resultant sulfide (III) may be oxidized to the sulfonyl compound (IV) by treatment with a conventional oxidizing agent, such as m-chloroperoxybenzoic acid, at −10° to 30° C. in a solvent at atmospheric pressure. The sulfonyl compound may be conventionally brominated to produce compound (V), then dehydrobrominated by contact with a base, such as sodium carbonate or a trialkylamine, in a solvent.

The sulfonyl propenyl bromide (VI) may be contacted with an appropriate phosphate salt (VII) in a solvent at atmospheric pressure to produce the compounds of the invention (I). The chemistry for preparation of phosphate salts (VII) is well known.

The following examples describe in detail methods which may be used to prepare compounds of the invention.

EXAMPLE 1

Preparation of 1-methylsulfonyl-3-bromo-prop-1-ene

Methyl mercaptan (106 g) was dissolved in 500 ml water and cooled to 0° C. A 50% solution of sodium hydroxide (160 g) was added dropwise, after which the solution was stirred at room temperature for one hour. Allyl bromide (242 g) was added in portions and the mixture was stirred overnight. After separation into layers, the organic layer was dried ($MgSO_4$), diluted with methylene chloride (2 liters) and cooled with a dry-ice acetone bath. The solution was kept between $-10°$ and 20° C. while adding 896 g m-chloroperbenzoic acid (85%) in portions. The mixture was refluxed for 2 hours.

The solids were filtered off and the filtrate was washed with sodium sulfite solution, sodium bicarbonate solution, dried ($MgSO_4$) and stripped to yield 136 g 3-methylsulfonyl-prop-1-ene (Product A).

Product A (60 g) was dissolved in 300 ml carbon tetrachloride and 80 g bromine was added dropwise. After refluxing for 30 minutes, the solvent was stripped. Yield 98 g of 1-methylsulfonyl-2,3-dibromopropane (Product B).

Product B (90 g), sodium carbonate (50 g) and 250 cc acetone were combined and refluxed for 4 hours. The mixture was filtered and the filtrate was stripped, dissolved in methylene chloride, washed with water, dried ($MgSO_4$) and stripped to yield an oil which solidified upon standing. Yield 60 g of the title product.

EXAMPLE 2

Preparation of S-(3-methylsulfonyl-prop-2-enyl)-O-methyl-phosphoramidothioate

1-Methylsulfonyl-3-bromo-prop-1-ene (5.97 g) was dissolved in 50 cc acetonitrile. Sodium O-methyl-phosphoramidothioate (4.5 g) was added and the mixture was stirred at room temperature overnight. The mixture was diluted with water and extracted with methylene chloride. The extract was dried ($MgSO_4$), stripped and slurried in ether-methylene chloride to yield the title product as a solid, mp 101°–102° C.

EXAMPLE 3

Preparation of S-(3-isobutylsulfonyl-prop-2-enyl)-0,0-dimethyl-phosphorothiolothionate 1-(Isobutylsulfonyl)-3-bromo-prop-1-ene was prepared in a manner analogous to the procedure of Example 1 using methanol as a solvent, and was dissolved (6 g) in 50 cc dimethoxyethane. Ammonium 0,0-diemthyl phosphorothiolthionate (4.3 g) was added and the mixture was stirred at room temperature for 3 hours. Work-up was accomplished as in Example 2. The product was purified by chromatography (10% Acetone:$CH_2Cl_2$) to yield 2.5 g of the title product.

According to procedures substantially similar to Example 3, the following reactants were combined to produce compounds of my invention.

| Reactant 1 | Reactant 2 | | | |
|---|---|---|---|---|
| $RSO_2-CH=CHCH_2Br$ | $M^+ {}^-S-P(=X)(Y)(Z)$ | | | |
| R | M | X | Y | Z |
| $n\text{-}C_4H_9-$ | $NH_4^+$ | S | $-OCH_3$ | $-OCH_3$ |
| phenyl | $NH_4^+$ | S | $-OC_2H_5$ | $-OC_2H_5$ |
| $C_2H_5-$ | $NH_4^+$ | O | $-OCH_3$ | $-OCH_3$ |
| $CH_3-$ | $NH_4^+$ | S | $-O(n\text{-}C_3H_7)$ | $-O(n\text{-}C_3H_7)$ |
| $CH_3-$ | $NH_4^+$ | S | $-O(i\text{-}C_3H_7)$ | $-O(i\text{-}C_3H_7)$ |
| $C_2H_5-$ | $K^+$ | O | $-OC_2H_5$ | phenyl |
| $C_2H_5-$ | $K^+$ | S | $-OC_2H_5$ | phenyl |
| $C_2H_5-$ | $K^+$ | S | $-OC_2H_5$ | $-C_2H_5$ |
| $C_2H_5-$ | $Na^+$ | O | $-OCH_3$ | $-NH_2$ |
| $C_2H_5-$ | $Na^+$ | O | $-OC_2H_5$ | $-NH_2$ |
| $i\text{-}C_3H_7-$ | $Na^+$ | O | $-OCH_3$ | $-NHCH_3$ |
| $C_2H_5-$ | $Na^+$ | O | $-OCH_3$ | $-NHC(=O)CH_3$ |
| $CH_3-$ | $Na^+$ | O | $-OCH_3$ | $-SCH_3$ |
| $CH_3-$ | $Na^+$ | O | $-OC_2H_5$ | $-SCH_3$ |
| $C_2H_5-$ | $Na^+$ | O | $-OC_2H_5$ | $-SC_2H_5$ |
| $CH_3-$ | $Na^+$ | O | $-OC_2H_5$ | $-S(i\text{-}C_3H_7)$ |

Insect Control

The compounds of the present invention are useful as insecticides, particularly on insects such as houseflies, cabbage looper, cotton aphids, alfalfa weevils, red flour beetles, mealworms, rootworms, American roaches and Yellow Fever Mosquitos.

The compounds are very potent and are used at extremely low concentrations. For example, compositions containing 100 ppm to 0.01 ppm, preferably from 5 ppm to 0.1 ppm, are effective for the control of insects. However, the effective concentration depends in part on the mode of application and the particular insect.

The compounds may be applied in either liquid or solid formulations to the pre-adult insects or their environment. For example, they may be sprayed or otherwise applied directly to plants or aqueous bodies so as to effect control of insects coming into contact therewith.

Formulations of the compounds of this invention will comprise a toxic amount of one or more of the compounds and a biologically inert carrier. Usually they will also contain a wetting agent. Solid carriers such as clay, talc, sawdust, alfalfa meal, and the like may be used in such formulations. Liquid diluents which may be used with these compounds include water with appropriate emulsifying agents and aromatic solvents. In addition, these formulations may contain other compatible pesticides, fillers, stabilizers, attractants, and the like.

The concentration of the active ingredient to be used with inert carriers, either solid or liquid carriers, will be dependent upon many factors, such as the particular compound which is used, the carrier in or upon which it is incorporated, the method and conditions of application, the insect species to be controlled, etc., the proper consideration of these factors being within the skill of those versed in the art. In general, the toxic ingredients of this invention will be effective in concentrations from about 0.0001% by weight to as high as 50% by weight, or higher.

The compounds of the invention are particularly useful in combination with mosquito larvicidal petroleum oil dispersions. Petroleum oils suitable as mosquito larvicidal dispersions are known. Such hydrocarbon oils include mineral oils such as naphthenic base and paraffinic base lubricating oils, etc., as well as synthetic oils. Such hydrocarbon oils are nonphytotoxic and generally contain not more than a few percent aromatics. Particularly suitable hydrocarbon oils have boiling points above 350° to 400° F. and viscosities from about 33 to 200 SSU at 100° F.

The amount of the compound of the invention employed in petroleum oil generally ranges from 0.1% to 10% by weight, based on weight of oil. The hydrocarbon oil dispersions containing the compounds of the invention are contacted with or applied to the surface of the aqueous bodies wherein mosquito control is desired by conventional methods.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insecta, but also to other related classes of arthropods whose members are segmented invertebrates having more or fewer than 6 legs, such as spiders, mites, ticks, centipedes, worms and the like.

FUNGICIDAL UTILITY

The compounds of the invention are useful for controlling fungi, particularly plant fungal infections. However, some fungicidal compositions of the invention may be more fungicidally active than others against particular fungi. For example, the activity of the preferred compounds of the invention is highly specific for certain fungal diseases such as downy mildews, e.g., *Plasmopara viticola* (grapes) and late blights, e.g., *septoria apii* (celery).

The compounds of the invention are particularly useful fungicides because they cure established fungal infections. This permits economical use of the fungicides of the invention, because they need not be applied to plants unless fungal infection actually occurs. Thus, a preventative program of applying fungicides against potential fungal infection is not necessary.

When used as fungicides, the compounds of the invention are applied in fungicidally effective amounts of fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5-80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, the example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of covercrop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

The insecticidal and fungicidal activity of the compounds of the invention are illustrated by the following examples.

EXAMPLE 4

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250 ppm suspension of the test compound in acetone, water and a small amount of a nonionic emulsifier. The sprayed plants were then inoculated one day later with the organism, placed in an environmental chamber and incubated at 66°-68° F. and 100% relative humidity for at least 16 hours. Following the incubation, the plants were maintained in a greenhouse at 60-80% relative humidity for approximately 7 days. The percent disease control provided by a given test compound was based on the percent disease reduction relative to untreated check plants. The results are tabulated in Table I. In Table I, the test concentration is 250 ppm unless otherwise indicated by the figures in parentheses.

EXAMPLE 5

Celery Late Blight

The celery late blight tests were conducted using celery (Utah) plants 11 weeks old. The celery late blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°-68° F. in 100% relative humidity for an extended period of time (approximately 48 hours). Following the incubation the plants were allowed to dry and then were maintained at a 60-80% relative humidity for approximately 14 days. The percent disease control provided by a given candidate toxicant is based on the percent disease reduction relative to untreated check plants. The results are reported in Table I.

EXAMPLE 6

Grape Downy Mildew Control

The compounds of the invention were tested for the control of the grape downy mildew organism *Plasmopara viticola*. Detached leaves, between 70 and 85 mm in diameter, a 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 18°-22° C. and about 100% relative humidity. Seven to nine days after inoculation, the amount of disease control was determined. The percent disease control provided by a given test compound was based on the percent disease reduction relative to untreated check plants. The results are tabulated in Table I.

EXAMPLE 7

Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250 ppm solution of the test compound in an acetone-and-water solution containing a small amount of a nonionic emulsifier. The sprayed plants were inoculated one day later with the organism, dried and maintained at 60-80% relative humidity for about 12 days. Percent disease control was based on the percent disease development on untreated check plants. The compounds tested and the results are tabulated in Table I.

EXAMPLE 8

Powdery Mildew

The powdery mildew test was made using bean seedlings (var. Bountiful) with well-developed primary leaves. The pathogen was *Erysiphe polygoni*. The bean seedlings were sprayed with a 250 ppm solution of the test compound in an acetone-water mixture containing a nonionic emulsifier. The treated plants were inoculated one day after spray application of the test compound with the pathogen. The plants were then maintained in a greenhouse at a 60-80% relative humidity and at a temperature of 68°-70° F. The rate of infection on the leaves was made after about 10 days. The percent disease control provided by a given test compound was based on the disease reduction relative to untreated check plants. The results are reported in Table I.

EXAMPLE 9

Leaf Rust

The leaf-rust was made using pinto beans. The pathogen was *uronyces phaseoli tipica*. The pinto-bean plants were sprayed with a 250 ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68°-70° F. The plants were then removed from the chamber, allowed to dry, and then maintained in a greenhouse at a 60-80% relative humidity. The rate of infection on the leaves was made after about 14 days. The percent disease control provided by a given test compound was based on the disease reduction relative to untreated check plants. The results are reported in Table I.

EXAMPLE 10

Mosquito Control

The compounds of the present invention were tested as insect growth regulator (IGR) insecticides against Yellow Fever Mosquito larvae (*Aedes aegypti*) by the following procedures: Late-fourth-stage larvae of the mosquito are placed in a cup containing 30 ml of deionized water containing a known amount of the test compound dissolved therein. About 20 larvae are used per test. The larvae are fed and allowed to pupate. The live pupae are kept until the adult mosquito emerges. A count is made at each step for mortality, i.e., larval, pupal and adult mortality. The compound tested, the concentration and the mortality counts are tabulated in Table II.

EXAMPLE 11

Cabbage Looper Control

The compounds of the invention were tested as insecticides and insect growth regulators (IGR) against the cabbage looper (*Trichoplusia ni*) by the following procedure: An acetone solution of candidate toxicant containing a small amount of nonionic emulsifier was diluted in water to 500 ppm. Cucumber leaf sections were dipped in the toxicant solution and dried to remove excess moisture. The treated leaf sections were then infested with 3rd stage cabbage looper larvae. Direct mortality readings on larvae were taken after 48 hours. Survivors of this test were then fed on semi-synthetic diet until they pupated and emerged as adults and during the course of their development readings were made for insect growth regulator activity. Direct larval mortality and insect growth regulator mortality results are tabulated in Table III.

In a second test, 5 microliters of an acetone solutions containing 10, 3, 1 and 1 micrograms of compound No. 40 were applied topically to the entire body length of late-fifth stage cabbage looper larvae.

The treated larvae were fed and allowed to pupate, emerge as adults, mate and lay eggs. Insect growth regulator activity and mortality were observed from the time of larval treatment through to the laying of eggs. The insect growth regulator activity of compound No. 40 on cabbage looper larvae, pupae, adults and eggs is tabulated in Table V.

EXAMPLE 12

Housefly Control

Houseflies (*Musca domestica* L.) A 500 ppm acetone solution of the candidate toxicant was placed in a microsprayer (atomizer). A random mixture of anesthetized male and female flies was placed in a container and 70 microliters of the above-described acetone solution was sprayed on them. A lid was placed on the container. A mortality reading was made after 24 hours. The results are tabulated in Table IV.

EXAMPLE 13

Aphid Control

Aphids (*Aphis gossypii* Glover): An acetone solution of the candidate toxicant containing a small amount of nonionic emulsifier was diluted with water to 40 ppm. Cucumber leaves infested with the cottom aphids were dipped in the toxicant solution. Mortality readings were then taken after 24 hours. The results are tabulated in Table IV.

EXAMPLE 14

Rootworm Control

The compounds of the present invention were tested as insecticides against the western spotted cucumber beetle (*Diabrotica u. undecimpunctata*) by the following procedure: 1.12 ml of an acetone solutions containing 11.2 mg of the test compound were mixed with 20 ml of 30 mesh (size 4) vermiculite, then thoroughly mixed with 825 grams of soil with 10% soil moisture. This gives a soil treatment of 15 ppm candidate compound, based on the toxicant to dry soil weight ration. 130 g batches of treated soil were placed in 8-ounce plastic cups together with 20–30 seven-day old Diabrotic eggs and 10 presoaked corn seeds. Tests were incubated for 10 days and the mortality of newly hatched larvae was read by visually observing the degree of corn root damage by feeding larvae in conjunction with the visible presence of live and/or dead larvae. The results are tabulated in Table IV.

EXAMPLE 15

American Cockroach Control

American Cockroach (*Periplaneta americana* L.): A 500 ppm acetone solution of the candidate toxicant was placed in a microsprayer (atomizer). A random mixture of anesthetized male and female roaches was placed in a container and 70 microliters of the above-described acetone solution was sprayed on them. A lid was placed on the container. A mortality reading was made after 24 hours. The results are tabulated in Table IV.

TABLE A

COMPOUNDS OF THE FORMULA $$R-SO_2-CH=CHCH_2-S-\underset{\underset{Z}{|}}{\overset{\overset{X}{\|}}{P}}-Y$$

| No. | R | X | Y | Z | mp °C. | C H N CALC | ANALYSIS FD |
|-----|---|---|---|---|--------|------------|-------------|
| 1 | $C_2H_5$ | O | $OCH_3$ | $NH_2$ | Oil | 27.79 5.44 5.40 | 29.4 5.88 6.17 |
| 2 | $i-C_4H_9$ | O | $OCH_3$ | $NH_2$ | 77–78 | 33.44 6.23 4.88 | 34.13 6.6 4.98 |
| 3 | $C_2H_5$ | O | $OC_2H_5$ | $NH_2$ | Oil | 30.76 5.90 5.13 | 31.49 6.12 5.29 |
| 4 | 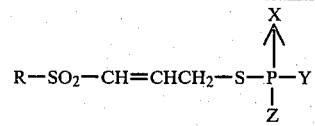 | O | $OCH_3$ | $NH_2$ | 84–85 | 38.20 6.41 4.46 | 38.98 6.56 4.62 |
| 5 |  | O | $OC_2H_5$ | $NH_2$ | Oil | 40.35 6.77 4.26 | 40.47 6.94 4.01 |
| 6 | $CH_3$ | O | $OCH_3$ | $NH_2$ | 101–102 | 24.48 4.93 5.71 | 23.92 4.51 4.95 |
| 7 | $CH_3$ | O | $OC_2H_5$ | $NH_2$ | Oil | 27.79 | 27.12 |

TABLE A-continued

COMPOUNDS OF THE FORMULA $$R-SO_2-CH=CHCH_2-S-\underset{\underset{Z}{|}}{\overset{\overset{X}{\uparrow}}{P}}-Y$$

| No. | R | X | Y | Z | mp °C. | C H N CALC | ANALYSIS FD |
|---|---|---|---|---|---|---|---|
|  |  |  |  |  |  | 5.44 | 5.35 |
|  |  |  |  |  |  | 5.40 | 4.49 |
| 8 | $C_2H_5$ | O | $OCH_3$ | $\underset{NHCCH_3}{\overset{O}{\|}}$ | Oil | 31.88<br>5.35<br>4.65 | 31.06<br>5.17<br>4.01 |
| 9 | n-$C_4H_9$ | O | $OCH_3$ | $\underset{NHCCH_3}{\overset{O}{\|}}$ | Oil | 36.46<br>6.12<br>4.25 | 37.42<br>5.93<br>4.07 |
| 10 | ⬡ | O | $OCH_3$ | $\underset{NHCCH_3}{\overset{O}{\|}}$ | Oil | 40.55<br>6.24<br>3.94 | 39.23<br>5.92<br>3.58 |
| 11 | $C_2H_5$ | O | $OCH_3$ | $N(CH_3)_2$ | Oil | 33.44<br>6.32<br>4.87 | 34.37<br>6.65<br>5.49 |
| 12 | i-$C_4H_9$ | O | $OCH_3$ | $NHCH_3$ | 85–87 | 35.87<br>6.69<br>4.65 | 36.35<br>6.75<br>4.87 |
| 13 | ⬡ | O | $OCH_3$ | $NHCH_3$ | 42–43 | 40.35<br>6.77<br>4.28 | 40.29<br>6.69<br>4.47 |
| 14 | $CH_3$ | O | $OCH_3$ | $NHCH_3$ | 95–96 | 27.79<br>5.44<br>5.40 | 27.5<br>5.37<br>5.17 |
| 15 | $CH_3$ | O | $OCH_3$ | $SCH_3$ | Oil | 26.07<br>4.74 | 25.74<br>4.59 |
| 16 | $C_2H_5$ | O | $OCH_3$ | $SCH_3$ | Oil | 28.95<br>5.21 | 30.38<br>5.35 |
| 17 | n-$C_4H_9$ | O | $OCH_3$ | $SCH_3$ | Oil | 33.94<br>6.01 | 33.7<br>5.86 |
| 18 | ⬡ | O | $OCH_3$ | $SCH_3$ | Oil | 38.35<br>6.15 | 36.02<br>5.78 |
| 19 | $CH_3$ | O | $OC_2H_5$ | $SC_2H_5$ | Oil | 31.56<br>5.63 | 31.28<br>5.64 |
| 20 | $C_2H_5$ | O | $OC_2H_5$ | $SC_2H_5$ | Oil | 33.95<br>6.01 | 33.55<br>6.0 |
| 21 | n-$C_4H_9$ | O | $OC_2H_5$ | $SC_2H_5$ | Oil | 38.13<br>6.69 | 42.74<br>7.3 |
| 22 | ⬡ | O | $OC_2H_5$ | $SC_2H_5$ | Oil | 41.91<br>6.76 | 40.14<br>6.8 |
| 23 | $C_2H_5$ | O | $OC_2H_5$ | $SCH_3$ | Oil | 31.56<br>5.63 | 32.92<br>5.68 |
| 24 | $CH_3$ | O | $OC_2H_5$ | $SCH_3$ | Oil | 28.95<br>5.21 | 29.53<br>5.45 |
| 25 | $CH_3$ | O | $OC_2H_5$ | $S(i-C_3H_7)$ | Oil | 33.95<br>6.01 | 33.83<br>6.23 |
| 26 | $C_2H_5$ | O | $OC_2H_5$ | $S(i-C_3H_7)$ | Oil | 36.13<br>6.37 | 36.36<br>6.62 |
| 27 | n-$C_4H_9$ | O | $OC_2H_5$ | $S(i-C_3H_7)$ | Oil | 39.98<br>6.99 | 41.01<br>7.14 |
| 28 | n-$C_4H_9$ | O | $OCH_3$ | ⬡ | Oil | 48.26<br>6.08 | 46.63<br>6.21 |
| 29 | $C_2H_5$ | O | $OC_2H_5$ | ⬡ | Oil | 46.69<br>5.73<br>19.18* | 41.93<br>5.72<br>22.2 |
| 30 | $C_2H_5$ | O | $OCH_3$ | ⬡ | Oil | 44.98<br>5.35 | 43.15<br>5.41 |
| 31 | $CH_3$ | O | $OC_2H_5$ | ⬡ | Oil | 44.98<br>5.35 | 45.75<br>5.37 |
| 32 | $CH_3$ | O | $OCH_3$ | ⬡ | Oil | 43.12<br>4.94 | 42.48<br>4.96 |
| 33 | n-$C_4H_9$ | O | $OCH_3$ | $OCH_3$ | Oil | 35.75<br>6.33 | 38.23<br>6.00 |
| 34 | $C_2H_5$ | O | $OCH_3$ | $OCH_3$ | Oil | 30.65<br>5.51 | 29.98<br>4.99 |

TABLE A-continued

COMPOUNDS OF THE FORMULA $$R-SO_2-CH=CHCH_2-S-\overset{\overset{\displaystyle X}{\uparrow}}{\underset{\underset{\displaystyle Z}{|}}{P}}-Y$$

| No. | R | X | Y | Z | mp °C. | C H N CALC | ANALYSIS FD |
|---|---|---|---|---|---|---|---|
| 35 | C6H5 (phenyl) | S | OC2H5 | OC2H5 | Oil | 41.91 6.76 | 42.38 6.91 |
| 36 | n-C4H9 | S | OC2H5 | OC2H5 | Oil | 38.13 6.69 | 38.62 6.92 |
| 37 | C2H5 | S | OC2H5 | OC2H5 | Oil | 33.94 6.01 | 34.1 6.53 |
| 38 | i-C3H7 | S | OC2H5 | OC2H5 | Oil | 36.13 6.37 | 37.76 6.41 |
| 39 | CH3 | S | OC2H5 | OC2H5 | Oil | 31.56 5.63 | 32.88 5.73 |
| 40 | i-C4H9 | S | OCH3 | OCH3 | Oil | 33.95 6.01 | 34.44 5.97 |
| 41 | i-C4H9 | S | OC2H5 | OC2H5 | Oil | 38.13 6.69 | 39.41 6.5 |
| 42 | CH3 | S | O(i-C3H7) | O(i-C3H7) | Oil | 36.13 6.37 | 36.48 6.67 |
| 43 | C2H5 | S | O(i-C3H7) | O(i-C3H7) | Oil | 38.13 6.69 | 37.41 6.89 |
| 44 | CH3 | S | O(n-C3H7) | O(n-C3H7) | Oil | 36.13 6.37 | 36.73 6.55 |
| 45 | C2H5 | S | O(n-C3H7) | O(n-C3H7) | Oil | 38.13 6.69 | 38.51 6.9 |
| 46 | n-C4H9 | S | O(n-C3H7) | O(n-C3H7) | Oil | 41.69 7.27 | 41.15 7.22 |
| 47 | C2H5 | S | OC2H5 | C6H5 (phenyl) | Oil | 44.55 5.46 | 44.29 5.39 |
| 48 | i-C3H7 | S | OC2H5 | C6H5 (phenyl) | Oil | 46.13 5.81 | 42.19 5.37 |
| 49 | CH3 | S | OC2H5 | C6H5 (phenyl) | Oil | 42.84 5.09 | 45.38 5.5 |
| 50 | i-C4H9 | S | OC2H5 | C6H5 (phenyl) | Oil | 47.59 6.13 | 48.16 6.39 |
| 51 | C2H5 | S | OC2H5 | C2H5 | Oil | 35.74 6.33 | 37.31 6.29 |
| 52 | CH3 | S | OC2H5 | C2H5 | Oil | 33.32 5.94 | 34.72 6.18 |
| 53 | i-C4H9 | S | OC2H5 | C2H5 | Oil | 39.98 7.02 | 41.6 7.25 |

*Sulfur

TABLE I

FUNGICIDAL EFFICACY % CONTROL

| No. | GDM | TLB | CLB | TEB | BR | PM |
|---|---|---|---|---|---|---|
| 1 | 29 | 0 | 23 | 7 | 0 | 0 |
| 2 | 0 | 0 | 33 | 8 | 50 | 0 |
| 3 | 0 | 0 | 64 | — | 0 | 0 |
| 4 | 8 | 11 | 57 | 0 | 0 | 0 |
| 5 | 13 | 0 | 37 | 0 | 0 | 0 |
| 6 | 44 | 0 | 44 | 0 | 0 | 0 |
| 7 | 14 | 0 | 14 | 0 | 0 | 0 |
| 8 | 0 | 0 | 0 | 0 | 0 | 0 |
| 9 | 13 | 0 | 0 | 0 | 0 | 0 |
| 10 | 0 | 0 | 0 | 0 | 4 | 0 |
| 11 | — | 0 | 28 | 0 | 0 | 0 |
| 12 | — | 0 | 50 | 23 | 0 | 0 |
| 13 | 29 | 0 | 23 | 0 | 50 | 0 |
| 14 | 0 | 0 | 29 | 21 | 23 | 0 |
| 15 | 14 | 0 | 44 | 39 | 0 | 0 |
| 16 | 44 | 0 | 29 | 71 | 0 | 0 |
| 17 | 14 | 0 | 69 | 0 | 0 | 0 |
| 18 | 79 | 0 | 44 | 0 | 0 | 0 |
| 19 | 0 | 0 | 18 | 0 | 7 | 18 |
| 20 | 0 | 0 | 18 | 21 | 11 | 0 |
| 21 | 6 | 0 | 0 | 21 | 0 | 0 |
| 22 | 13 | 0 | 0 | 21 | 0 | 0 |
| 23 | 8 | 0 | 0 | 0 | 4 | 18 |
| 24 | 8 | 35 | 0 | 0 | 4 | 18 |
| 25 | 18 | 0 | 21 | 0 | 18 | 0 |
| 26 | 0 | 0 | 56 | 11 | 0 | 11 |
| 27 | 0 | 0 | 35 | 42 | 0 | 33 |
| 28 | 0 | 44 | — | 0 | 0 | — |
| 29 | 0 | 0 | 0 | 0 | 0 | 11 |
| 30 | 0 | 0 | 50 | 45 | 18 | 39 |
| 31 | 0 | 0 | 50 | 0 | 0 | 0 |
| 32 | 0 | 0 | 23 | 42 | 0 | 0 |
| 33 | 11 | 0 | 44 | 0 | 0 | 6 |
| 34 | 6 | 0 | 23 | 0 | 0 | 0 |
| 35 | 23 | 18 | 90 | 0 | 0 | 0 |
| 36 | 11 | 0 | 84 | 0 | 0 | 0 |
| 37 | — | 0 | 13 | 0 | 0 | 0 |
| 38 | — | 0 | 23 | 27 | 0 | 0 |
| 39 | 0 | 6 | 23 | 0 | 0 | 0 |
| 40 | 96 | 0 | 50 | 83 | 0 | 23 |

TABLE I-continued

| | FUNGICIDAL EFFICACY % CONTROL | | | | | |
|---|---|---|---|---|---|---|
| No. | GDM | TLB | CLB | TEB | BR | PM |
| 41 | — | 37 | 3 | 0 | 0 | 36 |
| 42 | 6 | 0 | 0 | 0 | 8 | 0 |
| 43 | 0 | 35 | 0 | 0 | 0 | 18 |
| 44 | 18 | 0 | 56 | 62 | 18 | 11 |
| 45 | 29 | 0 | 21 | 0 | 0 | 0 |
| 46 | 42 | 0 | 39 | 93 | 18 | 37 |
| 47 | 13 | 4 | 65 | — | 0 | 11 |
| 48 | 6 | 50 | 37 | 6 | 35 | 0 |
| 49 | 0 | 0 | 50 | 89 | 0 | 23 |
| 50 | — | 37 | 12 | 0 | 0 | 4 |
| 51 | 0 | 4 | 42 | — | 4 | 23 |
| 52 | 0 | 0 | 50 | 42 | 0 | 0 |
| 53 | — | 23 | 12 | 0 | 0 | 10 |

GDM = Grape Downy Mildew (*Plasmopara viticola*)
TLB = Tomato Late Blight (*Phytophthora infestans*)
CLB = Celery Late Blight (*Septoria apii*)
TEB = Tomato Early Blight (*Alternaria solani*)
BR = Bean Rust (*Uronyces phaseoli*)
PM = Powdery Mildew (*Erysiphe polygoni*)

TABLE II

| | Yellow Fever Mosquito Control - % Mortality | | |
|---|---|---|---|
| | Direct % Mortality | IGR % Mortality | |
| No. | Larva | Pupa | Adult |
| 3 | 0 | 40 | 0 |
| 10 | 0 | 90 | 0 |
| 16 | 0 | 10 | 0 |
| 22 | 0 | 70 | 0 |
| 23 | 0 | 10 | 0 |
| 24 | 0 | 50 | 0 |
| 26 | 0 | 40 | 0 |
| 30 | 0 | 20 | 0 |
| 35 | 100 | 0 | 0 |
| 36 | 100 | 0 | 0 |
| 40 | 100 | 0 | 0 |
| 41 | 100 | — | — |
| 49 | 0 | 60 | 0 |
| 53 | 100 | — | — |

TABLE III

| | Cabbage Looper Control - at 500 ppm Dosage | | | |
|---|---|---|---|---|
| | | IGR % Mortality | | |
| No. | 48-Hr. Direct % Mortality | Larva | Pupa | Adult |
| 1 | 10 | 0 | 0 | 0 |
| 6 | 10 | 0 | 0 | 0 |
| 8 | 50 | 0 | 0 | 0 |
| 9 | 90 | — | — | — |
| 10 | 90 | 0 | 0 | 0 |
| 12 | 0 | 0 | 10 | 0 |
| 13 | 0 | 0 | 0 | 10 |
| 19 | 40 | 0 | 0 | 0 |
| 20 | 70 | 0 | 0 | 0 |
| 21 | 70 | 0 | 0 | 0 |
| 22 | 90 | 0 | 0 | 0 |
| 23 | 100 | — | — | — |
| 24 | 20 | 0 | 0 | 0 |
| 25 | 100 | — | — | — |
| 26 | 100 | — | — | — |
| 27 | 80 | 0 | 0 | 0 |
| 28 | 100 | 0 | 0 | 0 |
| 29 | 60 | 0 | 0 | 0 |
| 30 | 70 | 0 | 0 | 0 |
| 31 | 100 | 0 | 0 | 0 |
| 32 | 100 | 0 | 0 | 0 |
| 34 | 10 | 0 | 0 | 0 |
| 35 | 80 | 0 | 0 | 0 |
| 36 | 50 | 0 | 0 | 0 |
| 38 | 20 | 0 | 0 | 0 |
| 40 | 10 | 0 | 0 | 0 |
| 41 | 50 | 0 | 0 | 0 |
| 44 | 0 | 0 | 10 | 0 |
| 45 | 0 | 0 | 0 | 12 |
| 47 | 0 | 0 | 0 | 10 |
| 51 | 100 | 0 | 0 | 0 |
| 52 | 40 | 0 | 0 | 0 |
| 53 | 60 | 0 | 0 | 0 |

TABLE IV

| | % Mortality | | | |
|---|---|---|---|---|
| No. | Aphid (40 ppm) | Housefly (500 ppm) | Am. Roach (500 ppm) | Rootworm (15 ppm) |
| 1 | 90 | 100 | 90 | 0 |
| 2 | 98 | 0 | 0 | 0 |
| 6 | 15 | 96 | 15 | 0 |
| 7 | 78 | 96 | 0 | 0 |
| 8 | 70 | 100 | 60 | 0 |
| 9 | 39 | 100 | 60 | 0 |
| 10 | 78 | 100 | 100 | 0 |
| 15 | 70 | 90 | 60 | 0 |
| 16 | 60 | 0 | 0 | 0 |
| 19 | 0 | 0 | 96 | 0 |
| 20 | 0 | 0 | 0 | 96 |
| 23 | 90 | 0 | 100 | 99 |
| 24 | 78 | 99 | 98 | 0 |
| 25 | 90 | 99 | 50 | 96 |
| 26 | 94 | 99 | 70 | 0 |
| 27 | 15 | 39 | 15 | 0 |
| 28 | 0 | 15 | 0 | 0 |
| 30 | 11 | 0 | 0 | 0 |
| 31 | 39 | 0 | 0 | 0 |
| 33 | 39 | 90 | 22 | 0 |
| 34 | 78 | 80 | 99 | 94 |
| 35 | 22 | 0 | 0 | 0 |
| 36 | 94 | 60 | 0 | 99 |
| 37 | 90 | 0 | 0 | 100 |
| 38 | 0 | 0 | 0 | 100 |
| 39 | 99 | 0 | 0 | 100 |
| 40 | 0 | 0 | 0 | 96 |
| 41 | 90 | 39 | 0 | 98 |
| 42 | 39 | 0 | 0 | 0 |
| 43 | 60 | 0 | 0 | 0 |
| 45 | 39 | 0 | 0 | 0 |
| 47 | 30 | 0 | 0 | 0 |
| 48 | 22 | 0 | 0 | 0 |
| 49 | 60 | 0 | 0 | 0 |
| 51 | 30 | 0 | 39 | 0 |
| 52 | 90 | 0 | 22 | 99 |
| 53 | 78 | 0 | 0 | 78 |

TABLE V

The insect growth regulator activity of compound No. 40 when topically applied to late-fifth stage cabbage looper larvae.

| Micrograms per larva | % Mortality | | | |
|---|---|---|---|---|
| | Larvae | Pupae | Adult | Eggs |
| 10 | 0 | 85 | 5 | No eggs |
| 3 | 0 | 50 | 5 | 100 |
| 1 | 0 | 0 | 0 | 100 |

What is claimed is:

1. A compound of the formula:

$$R-SO_2-CH=CHCH_2S-\overset{\overset{\displaystyle S}{\displaystyle \uparrow}}{\underset{\displaystyle Z}{P}}-Y$$

wherein R is alkyl of 1 to 6 carbon atoms, cycloalkyl of 5 to 10 carbon atoms, alkenyl of 2 to 6 carbon atoms, alkynyl of 2 to 6 carbon atoms, all of said R groups being optionally substituted with from 1 to 13 halogen atoms;

Y is $-OR^1$ or $-SR^1$ wherein $R^1$ is selected from the same groups which define R above;

Z is $-OR^2$ or $-SR^2$ wherein $R^2$ is selected from the same groups which define R above.

2. A compound according to claim 1 wherein Y is $OR^1$, Z is $-OR^2$ and R is alkyl of 1 to 6 carbon atoms.

3. A compound according to claim 2 wherein R is isopropyl and $R^1$ and $R^2$ are methyl.

4. A compound according to claim 2 wherein R is isobutyl and $R^1$ and $R^2$ are methyl.

* * * * *